US008639004B2

(12) United States Patent
McLean et al.

(10) Patent No.: US 8,639,004 B2
(45) Date of Patent: Jan. 28, 2014

(54) METHOD FOR PERFORMING MICRO-PERIMETRY EXAMS BASED ON A RETINAL VOLUME IMAGE AND A WELL REGISTERED FUNDUS IMAGE

(75) Inventors: Duncan McLean, Kingston (CA); Justin Pedro, Kingston (CA); John Rogers, Canterbury (GB)

(73) Assignee: Optos plc (GB)

( * ) Notice: Subject to any disclaimer, the term of this patent is extended or adjusted under 35 U.S.C. 154(b) by 548 days.

(21) Appl. No.: 12/866,953

(22) PCT Filed: Dec. 10, 2008
(Under 37 CFR 1.47)

(86) PCT No.: PCT/CA2008/002144
§ 371 (c)(1),
(2), (4) Date: Mar. 21, 2011

(87) PCT Pub. No.: WO2009/073970
PCT Pub. Date: Jun. 18, 2009

(65) Prior Publication Data
US 2012/0002856 A1    Jan. 5, 2012

Related U.S. Application Data

(60) Provisional application No. 61/012,526, filed on Dec. 10, 2007.

(51) Int. Cl.
*G06K 9/00* (2006.01)
(52) U.S. Cl.
USPC ......................................................... 382/131

(58) Field of Classification Search
USPC ........... 382/128, 131; 128/922; 351/200, 206, 351/209, 222, 224; 348/78; 600/452; 378/4, 378/6, 8, 12, 21
See application file for complete search history.

(56) References Cited

U.S. PATENT DOCUMENTS

| 6,227,667 B1* | 5/2001 | Halldorsson et al. .......... 351/206 |
| 6,247,812 B1* | 6/2001 | Miehle et al. ................. 351/206 |
| 7,593,559 B2* | 9/2009 | Toth et al. ..................... 382/128 |
| 2003/0157464 A1* | 8/2003 | Tanassi et al. ................. 434/81 |
| 2006/0187462 A1* | 8/2006 | Srinivasan et al. ............ 356/479 |
| 2007/0025642 A1* | 2/2007 | Buckland et al. ............. 382/294 |
| 2007/0070295 A1 | 3/2007 | Tsukada et al. |
| 2007/0115481 A1* | 5/2007 | Toth et al. ..................... 356/511 |

(Continued)

FOREIGN PATENT DOCUMENTS

JP       2007181537 A     7/2007

OTHER PUBLICATIONS

Menke, et al, "Combined use of SLO microperimetry and OCT for retinal functional and structural testing," Greafe's Archive for Clinical and Experimental Ophthalmology, 2006, pp. 634-638, vol. 244, Springer-Verlag.

(Continued)

*Primary Examiner* — Jason Repko
*Assistant Examiner* — Shervin Nakhjavan
(74) *Attorney, Agent, or Firm* — Laubscher & Laubscher, P.C.

(57) ABSTRACT

A method of performing a retinal examination is described wherein perimetry points are selected in three dimensional imaging data of the retinal tissue. The corresponding points in register with these perimetry points are mapped to an en-face image. These corresponding points are used as stimulus locations for a micro-perimetry examination.

3 Claims, 2 Drawing Sheets

(56) References Cited

U.S. PATENT DOCUMENTS

2007/0195269 A1* 8/2007 Wei et al. .................. 351/221
2007/0216909 A1* 9/2007 Everett et al. .............. 356/479
2008/0100612 A1* 5/2008 Dastmalchi et al. ........ 345/418

OTHER PUBLICATIONS

Midena, Chapters 2.1, 3.1 and 3.3, Perimetry and the Fundus an Introduction to Microperimetry, 2007, Slack Inc.

Podoleanu et al, "OCT En-face Images from the Retina with Adjustable Depth Resolution in Real Time," IEEE Journal of Selected Topics in Quantum Electronics, Jul./Aug. 1999, pp. 1176-1184, vol. 5 No. 4, IEEE.

Bradu, et al, "High-speed En-face Optical Coherence Tomography System for the Retina," Journal of Optoelectronics and Advance Materials, Dec. 2005, pp. 2913-2918, vol. 7 No. 6.

* cited by examiner

METHOD FOR PERFORMING MICRO-PERIMETRY EXAMS BASED ON A RETINAL VOLUME IMAGE AND A WELL REGISTERED FUNDUS IMAGE

FIELD OF THE INVENTION

This invention relates to the field of ophthalmogical diagnostic testing, and in particular to a method of performing micro-perimetry.

BACKGROUND OF THE INVENTION

Micro-perimetry is a well known diagnostic test used in ophthalmology for testing a patient's visual function. Stimuli are presented to a region of interest in order to test its optical responsiveness. All micro-perimetry tests are based on some sort of fundus image either from a scanning laser ophthalmoscope (SLO), fundus video camera or some other similar technology. The fundus of an eye is the interior surface of the eye, opposite the lens, and includes the retina, optic disc, macula, and posterior pole.

Using a fundus image the operator can place either standard perimetry patterns or manually created perimetry patterns. When attempting to test visual function the operator can use the fundus image to place perimetry points around what can be seen as potential problem areas. This technique is extremely limited in that many pathologies are not visible in a fundus image; instead the pathology may only be visible when a volume of retinal tissue is imaged, that is the retinal tissue is viewed in section.

SUMMARY OF THE INVENTION

In accordance with the present invention, three-dimensional volume imaging information obtained using three dimensional imaging equipment is scanned by the operator to select points of interest. The corresponding points are then mapped to a corresponding en-face image of the fundus or regions of interest. Optical coherence tomography (OCT) is ideally suited for gathering this type of volume information. However, any other technology that can gather retinal volume information can be used; for example MRI would also work.

Optical Coherence Tomography (OCT) is a scanning technique can be used to gather reasonably dense retinal tissue information. OCT is described, for example, U.S. Pat. No. 6,769,769, the contents of which are herein incorporated by reference, and permits a three dimensional image of the retina of the eye to be obtained.

Micro-perimetry needs some sort of fundus image in order to track patient eye movement so stimulus presentation is consistently located in the same location. After the operator has looked through the volume information to find points of interest to test with micro-perimetry and selected these areas of interest in the retinal volume image, and then mapped these point to corresponding locations on the fundus, the micro-perimetry examination can begin. To do this a fundus image that is aligned perfectly, or at least very well, with underlying retinal volume image is required. The mapping can be performed automatically by the computer or manually by the operator.

A fundus photo or fundus video image would work well for this. An SLO image from a combined SLO-OCT machine would be ideal for its high detail and nearly automatic registration to a retinal volume OCT image.

BRIEF DESCRIPTION OF THE DRAWINGS

The invention will now be described in more detail, by way of example only, with reference to the accompanying drawings, in which.

DETAILED DESCRIPTION OF PREFERRED EMBODIMENT

Figure 1:
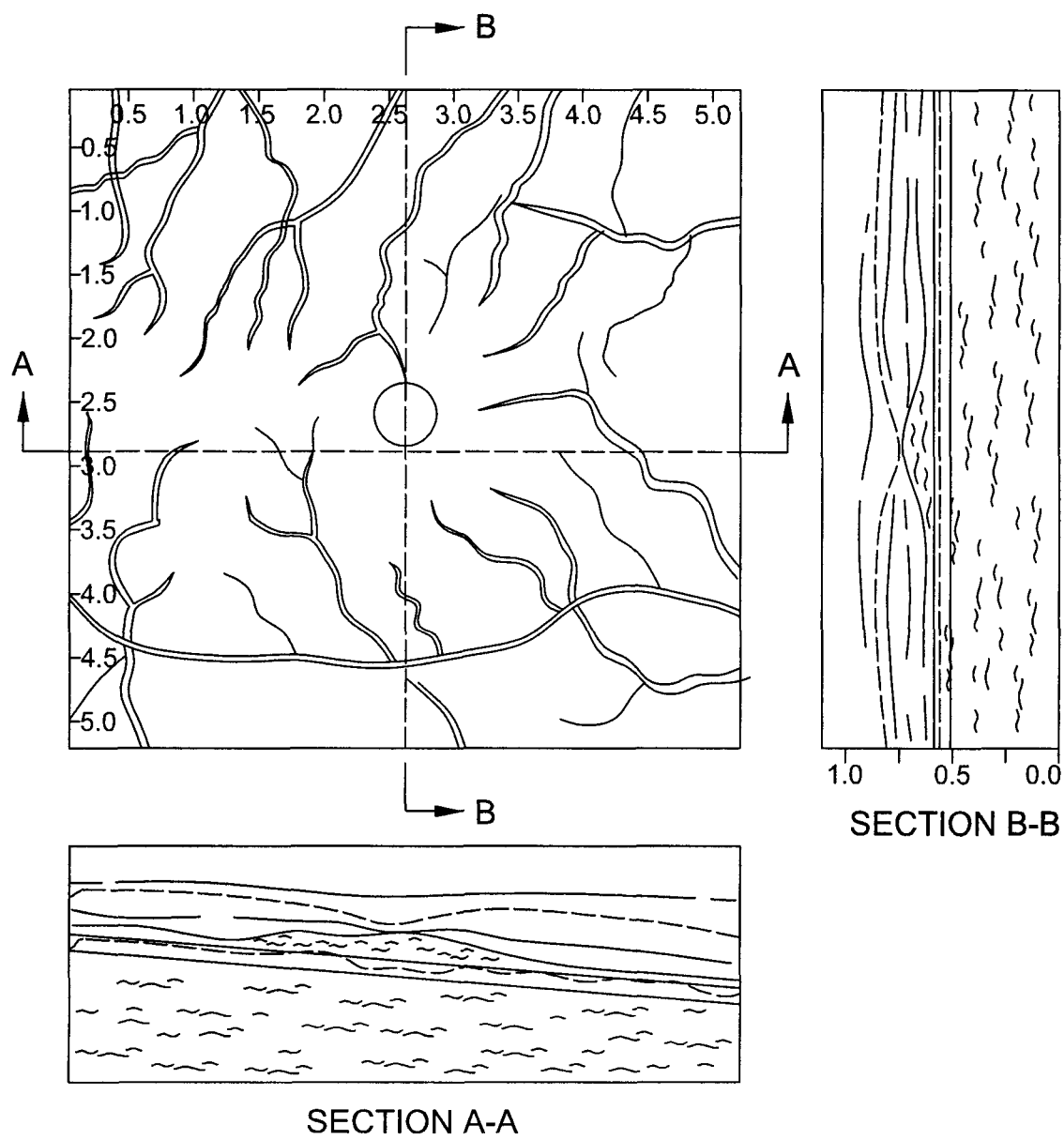
FIG. 1 is a dual SLO/OCT image showing volume information together with an overlying fundus image.

FIG. 1 shows an en-face image of the fundus of an eye, with sectional images obtained by OCT shown beside and below the en-face image. The image to the right is a cross section taken along the vertical axis, and the image below is a cross section taken along the horizontal axis. Such an image can be displayed on the display screen of OCT equipment.

In the case of SLO/OCT apparatus, the en-face image is obtained using SLO (scanning laser ophthalmoscope), whereas the sectional images are obtained by OCT.

In operation, the operator looks at the sectional OCT images to the right and below the main image to find points of interest, for example, particular points where some pathological condition may be noted. He or she then selects these points, for example, by pointing to them and clicking with a mouse. The computer forming part of the OCT equipment then automatically places marks (indicated by an X) at these points in the sectional images, and makes corresponding points appear on the en-face fundus image. This can be achieved with a computer in standard OCT/SLO equipment, for example the dual OCT/SLO analyzer sold by Ophthalmic Technologies Inc (OTI).

Figure 2:
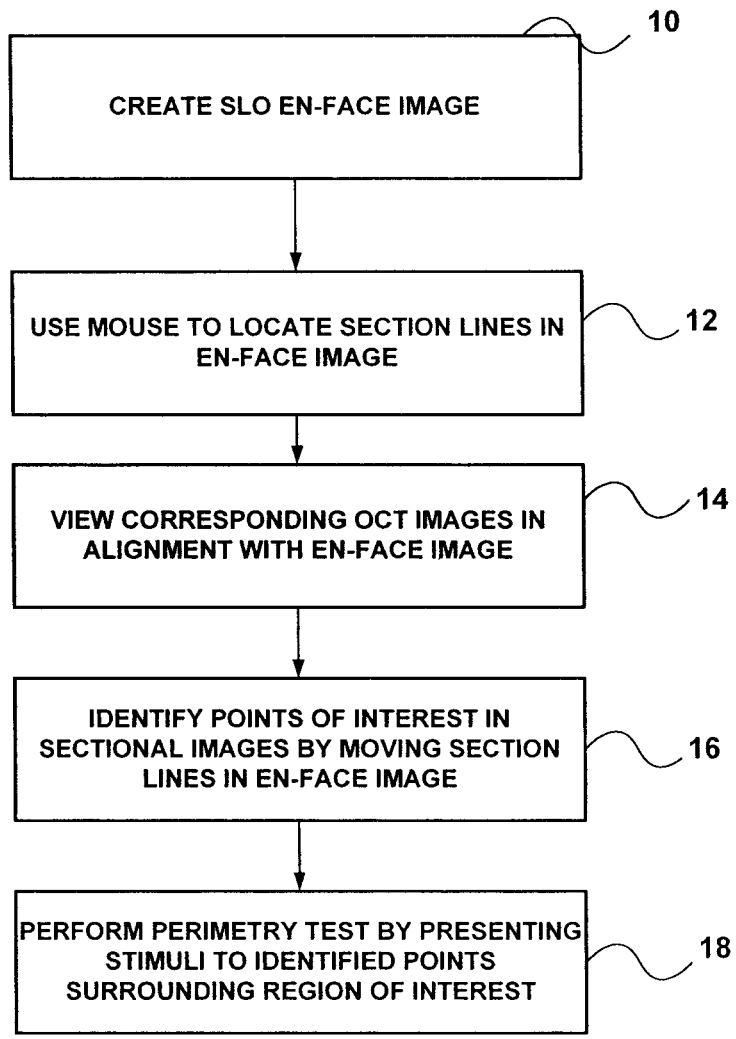
FIG. 2 is a flow diagram illustration the operation of the method in accordance with the invention.

FIG. 2 illustrates the steps involved in performing a micro-perimetry examination. At step 10, the operator creates an SLO en-face image of the retina using the dual OCT/SLO equipment. At step 12, the operator uses the mouse to locate the section lines on the en-face image. The dual OCT equipment then shows a corresponding sectional view alongside the en-face image. The vertical section is shown to the right and the horizontal section is shown below. Moving the mouse moves the section lines horizontally and vertically over the image.

At step 14, the operator views the corresponding OCT images in alignment with the en-face image to look for points of interest. At step 16, the operators then moves the section lines, looking at the corresponding sectional images, to identify additional points of interest, marking the points on the en-face image so that they are mapped to the points identified on the sectional images.

At step 18, the operator then performs a conventional perimetry test be presenting stimuli to the points that have been identified as being of interest on the en-face image, using the sectional images.

In alternative embodiment, the operator may map the points in the sectional images manually to the corresponding points in the en-face image.

The operator then uses the perimetry marks surrounding the region of interest in the en-face image as a basis for performing a standard perimetry test.

What is claimed is:

1. A computer-implemented method of performing a retinal examination, comprising:
   obtaining an en-face image of the fundus of an eye with a scanning laser ophthalmoscope;
   displaying the en-face image to an operator;

displaying operator-movable section lines on said en-face image;

obtaining sectional images along said displayed section lines using optical coherence tomography;

simultaneously displaying said sectional images alongside and in alignment with said en-face image;

accepting operator input to mark points of interest on said sectional images;

automatically displaying said points of interest at corresponding points on said en-face image so that they are mapped to the marked points on said sectional images; and presenting said corresponding points on said en-face image as stimulus locations for a micro-perimetry examination.

2. The method of claim 1, wherein said en-face images and sectional images are obtained with a dual Scanning Laser Ophthalmoscope/Optical Coherence Tomography apparatus.

3. The method of claim 1, wherein the operator-movable section lines are responsive to mouse movements.

\* \* \* \* \*